(12) United States Patent
Vanmaele et al.

(10) Patent No.: US 6,562,411 B2
(45) Date of Patent: May 13, 2003

(54) COMBINATORIAL COATING FOR DEVELOPING NOVEL MATERIALS

(75) Inventors: Luc Vanmaele, Lochristi (BE); Guido Desie, Herent (BE)

(73) Assignee: AGFA-Gevaert, Mortsel (BE)

( * ) Notice: Subject to any disclaimer, the term of this patent is extended or adjusted under 35 U.S.C. 154(b) by 0 days.

(21) Appl. No.: 09/848,613

(22) Filed: May 3, 2001

(65) Prior Publication Data

US 2002/0025380 A1 Feb. 28, 2002

Related U.S. Application Data

(60) Provisional application No. 60/206,773, filed on May 24, 2000.

(51) Int. Cl.[7] .............................. B05D 1/18; B05D 1/28; B05D 1/30; B05D 1/36; B05D 1/38
(52) U.S. Cl. ..................... 427/402; 427/8; 427/373.2; 427/407.1; 427/420; 427/428; 427/430.1
(58) Field of Search .................... 427/402, 8, 372.2, 427/407.1, 420, 428, 430.1

(56) References Cited

U.S. PATENT DOCUMENTS

| | | | | |
|---|---|---|---|---|
| 3,928,661 A | | 12/1975 | Higbee et al. ............... 427/259 |
| 4,132,357 A | * | 1/1979 | Blackinton .................... 239/11 |
| 5,776,359 A | * | 7/1998 | Schultz et al. ........... 252/62.51 |
| 5,985,356 A | | 11/1999 | Schultz et al. .................. 427/8 |
| 6,004,617 A | | 12/1999 | Schultz et al. .................. 427/8 |
| 6,030,917 A | | 2/2000 | Weinberg et al. ........... 502/104 |
| 6,034,775 A | | 3/2000 | McFarland et al. .......... 356/364 |
| 6,365,034 B1 | * | 4/2002 | Spellane ................... 205/775.5 |

FOREIGN PATENT DOCUMENTS

WO 9847613 10/1998 ............ B01J/19/00

OTHER PUBLICATIONS

Bernd Jandeleit, Combinatorial Materials Science Catalysis, Angew Chem. Int. Ed. 1999, 38, 2494–2532, 2495–2532.

Ted X. Sun, Combinatorial Search for Advanced Luminescience Materials, Biotec. and BioEng. vol. 61, No. 4 1998/1999 p. 193–201.

\* cited by examiner

*Primary Examiner*—Michael Barr
*Assistant Examiner*—Elena Tsoy
(74) *Attorney, Agent, or Firm*—Joseph T. Guy; Nexsen Pruet Jacobs & Pollard, LLC

(57) ABSTRACT

Methods and apparatus for rapid screening of layered materials, for a useful property. In the method at least two layered materials are applied on one single substrate. Preferably the materials are applied by coating from a coating composition and are multi-layered materials having at least two distinct layers.

4 Claims, 2 Drawing Sheets

COMBINATORIAL COATING FOR DEVELOPING NOVEL MATERIALS

The application claims the benefit of U.S. Provisional Application No. 60/206,773 filed May 24, 2000.

FIELD OF THE INVENTION

This invention relates to a method for the parallel development and screening of novel materials with coated layers having useful properties that need to be identified very rapidly. It further relates to apparatus for practising the method.

BACKGROUND OF THE INVENTION

When coated materials have to be produced, it is often necessary to apply various layers on top of each other. Most of the time it is desired that the ingredients of the layers do not intermix during coating. Coated materials that can be prepared in this way include inter alia ink jet receptive media, electrophotographic receptive media, photographic films, conductive films, food products such as biscuits and chocolates, multi-layer automotive coatings, paper products, such as packaging materials and paper towels, conductive films, X-ray screens, diagnostic materials such as diagnostic strips, etc.

New products, in the areas described above, need to be brought to the marketplace rapidly in a world of increasing competition and ever shortening lifecycles. Enormous pressure remains on R&D in order to test out different material combinations in a period of time that is as short as possible. Traditional methods of experimenting often lead to materials with useful properties that come to the market too late. In traditional chemical industries this dilemma has been tackled by the introduction of new approaches that can accelerate e.g. the discovery process of new drugs compared with traditional ways of experimenting. The approach of combinatorial chemistry and high-throughput screening methods is extremely powerful for investigating problems in a multi-dimensional space for materials whose properties can rely upon a very large number of parameters.

In the chemical field this combinatorial process involves the design and synthesis of high-density discovery libraries aimed at exploring large numbers of structurally or compositionally diverse compounds thought to have a significant chance of ruling the characteristics of the end product, but for which the conventional number of experiments to set up to screen all these components for useful properties is too large to be conducted. By combinatorially varying ingredients, process and reaction conditions, the total number of experiments one can screen rises exponentially, which drastically increases the chances of identifying a new material with interesting new and desired properties.

In recent years combinatorial chemistry methodologies have been increasingly applied to the field of materials science, including homogeneous and heterogeneous catalysis, phosphors for luminescent materials, etc . . . An excellent review has been presented by Jandeleit et al., Angew. Chem. Int. Ed., 1999, 38, 2494–2532. Many references to material design by combinatorial techniques can be found in this review. Combinatorial search for advanced luminescence materials has also been described in Biotech. & Bioeng. (Combinatorial Chemistry), vol. 61, no. 4, pp. 193–201. Combinatorial techniques for developing new materials have also been extensively used in the patent literature: e.g. U.S. Pat. No. 5,985,356, U.S. Pat. No. 6,004,617, U.S. Pat. No. 6,030,917, U.S. Pat. No. 6,043,363, U.S. Pat. No. 6,045,671 and U.S. Pat. No. 6,034,775.

In all of these prior art descriptions of combinatorial experimental material designs, different reaction components are applied to certain regions of a substrate using sol-gel chemistry or vapour deposition coating techniques, followed by thermal treatment procedures, e.g. annealing, to produce the final product, thereby losing the coated layer structure. See, e.g., U.S. Pat. No. 5,985,356, U.S. Pat. No. 6,004,617, U.S. Pat. No. 6,030,917 and U.S. Pat. No. 6,034,775 and references cited therein for such examples.

For many applications, as described above, more than 1 coating layer, is required, one located above the other, without mixing the ingredients in adjacent coating layers and maintaining its layered structure, e.g., photographic film in which multiple layers are present, such as silver negative films comprising typically at least 7 layers that may not be intermixed. The optimisation for these kind of materials is a very laborious and time consuming task in which many different coatings have to be applied and analysed. Once finished, said materials can be screened using high throughput procedures for useful properties including, e.g., electrical, optical, physicochemical, thermal, magnetic, mechanical, chemical, morphological, physical properties etc . . .

A method for speeding up the development of multi-layered coatings by incorporating the basic ideas of combinatorial chemistry would be very welcome.

OBJECTS AND SUMMARY OF THE INVENTION

It is an object of the invention to provide a method for speeding up the development of coated materials by applying an array of various coatings on predefined regions of a single substrate.

It is a further object of the invention to provide a method for speeding up the development of multi-layered materials wherein several variants of multi-layered materials can be prepared and screened for useful properties in parallel by applying an array of various multi-layer materials on pre-defined regions of a single substrate.

It is a further object of the present invention to combine a method for preparing an array of various coated materials on predefined regions of a single substrate with a method for rapid parallel screening for useful properties including, e.g., electrical, optical, physicochemical, thermal, magnetic, mechanical, chemical, morphological, physical properties, etc . . . Further objects and advantages of the invention will become clear from the detailed description herein after.

The objects of the invention are realised by a method for developing layered materials, comprising the steps of:

applying, on a first region, $R_M$, of a substrate, a first layered material, $MR_M$, and on a second region, $R_N$, of said substrate a second layered material, $MR_N$, said material, $MR_M$, being different from said material, $MR_N$, and screening said materials, $MR_M$ and $MR_N$, for a useful property, wherein said layers are applied by coating from a coating solution.

DETAILED DESCRIPTION OF THE INVENTION

Figure 1:
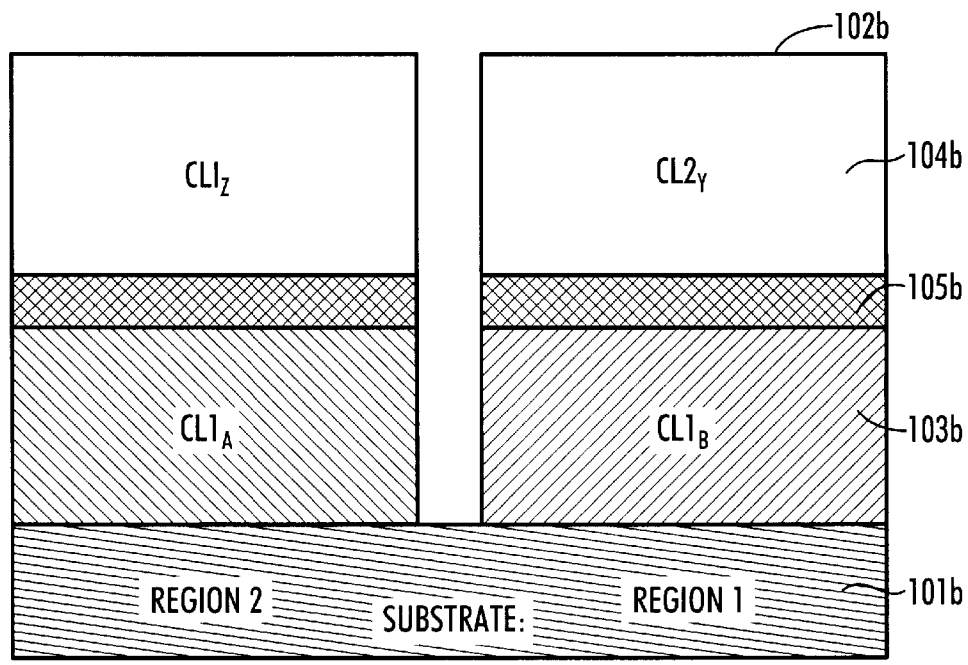
FIG. 1 shows schematically a cross-section of a substrate with two multi-layer coated materials, each having two distinct layers, coated in a single direction.

The following terms are intended to have the following general meanings as they are used throughout this document, not necessary being equivalent to certain terms used in typical literature descriptions:

Substrate: A material having a rigid or semi-rigid surface whereon layers are coated. In many embodiments, at least one surface of the substrate will be substantially flat. In some embodiments it may be desirable to physically separate regions whereon the different materials are coated. This can be done by including , for example, dimples, wells, raised regions, etched trenches, or the like. In some embodiments, the surface of the substrate itself contains wells, raised regions, etched trenches, etc. which form all or part of the regions whereon the different materials are coated. According to other embodiments, small beads or pellets may be provided on the surface within dimples or on other regions of the surface or, alternatively, the small beads or pellets may themselves be the substrate.

The surface area of the substrate is basically determined by the particular application. When, e.g. the method is used for the development of ink receiving layers for use in ink-jet, it can be beneficial to coat the different materials on different regions of a substrate with dimensions according to DIN A4, so that the different materials on the single substrate can easily be screened in parallel for their ink-receiving properties in a simple office ink-jet printer. When, e.g., the method is used for developing a photographic material, it can be beneficial to coat the different materials on different regions of a substrate with dimensions chosen so that an even exposure of all materials on the single substrate to light is possible in one exposure step without needing sophisticated optics. Although the actual size is application dependent, it will typically have a surface area of about 1 to 750 $cm^2$, usually about 10 to 300 $cm^2$.

Not only the dimensions of the substrate, but also the nature of the substrate depends on the application. It can be an organic homopolymer as well as an organic copolymer, e.g., polycondensation polymers as polyethyleneterephthalate, polyethylenenaphthalate, polyimide, polyamide, polycarbonate and copolymers thereof or addition polymers as polyacrylate, polystyrene, copolymers thereof. It can be paper, coated paper, cardboard, etc . . . It can be an inorganic substrate, e.g. a Si-wafer, glass, metal, etc . . . It can be textile and even foodstuff, e.g. a baked dough when it is intended to use the method of this invention to screen various coated layers of, e.g., chocolate or sugar, for use on cookies. When the method is, e.g., used for development of toner receiving layer for preparing transparencies by electrophotographic printing, it is known that a substrate for such a layer has to have high transparency and thermostability , and thus when using the method of this invention to develop such a material, the substrate in the method will also be chosen on the basis of the transparency and thermostability thereof.

Predefined Region: A predefined region is a localised area on a substrate which is, was, or is intended to be used for formation of a selected resulting material with a coated layer and is mostly referred to herein simply a "region". The "regions" on the substrate may be adjacent so that the coated layers touch each other at the borders of regions. When there is a risk that at the border some interaction between the layers can take place, then the area of regions is chosen so that the distance from border to border is large enough so that, notwithstanding some interaction at the borders, enough distinct material remains in the region for screening purposes. As described above, when there is a risk that at the border some interaction between the layers can take place, the regions on the substrate can be simply spaced as shown in FIG. 1, or can be separated physically by including , for example, dimples, wells, raised regions, etched trenches, or the like. When the regions are spaced, the spacing between them can range from 1 μm up to 50 cm, the width of the spacing depending of the application. The predefined region may have any convenient shape, e.g., linear, circular, rectangular, elliptical, wedge-shaped, etc. In some embodiments, a predefined region and, therefore, the area upon which each distinct material is deposited is smaller than about 25 $cm^2$, preferably less than 10 $cm^2$, more preferably less than 5 $cm^2$, even more preferably less than 1 $cm^2$, still more preferably less than 1 $mm^2$, and even more preferably less than 0.5 $mm^2$. In most preferred embodiments, the regions have an area less than about 10,000 $\mu m^2$, preferably less than 1,000 $\mu m^2$, more preferably less than 100 $\mu m^2$, and even more preferably less than 10 $\mu m^2$.

Conditioning: any treatment given to the coated layers after the coating thereof. The conditioning of the layers on the substrate can be a general conditioning or an individualised conditioning: all layers on the single substrate can be treated equally or every layer can be treated with a dedicated conditioning. The conditioning can proceed between the coating of the layers, after all layers are coated. E.g. when in the method of this invention a material with three layers is coated on a region of the substrate, there can be included a conditioning step after every coating, after two coatings, etc., all combinations can be used, dependent on the application. The conditioning can include the treatment with energy which may be selectively applied to one or more layers. "Energy" includes thermal energy, mechanical energy, electromagnetic energy having a wavelength between $10^{-14}$ and $10^4$ meter, e.g., electron beam radiation, gamma radiation, x-ray radiation, ultraviolet radiation, visible light, infrared radiation, microwave radiation and radio waves, etc . . . Also "pre-treated" air that is blown over said regions is implied by this conditioning. Air with specific humidity and temperature can be blown over said regions at a certain velocity, causing evaporation of ingredients of said multi-layer coating. Conditioning can also mean that the coated layers on the regions of the substrate are exposed to environmental conditions: e.g. Relative Humidity (RH) and Temperature profiles, but also atmospheres of reacting species such as formaldehyde hardener smog, etc.

Material: The term "material" is used herein to refer to the layer or combination of layers that have been coated onto a predefined region of a substrate. When the material comprises a combination of layers on top of each other these layers must be distinct. This means that when making a cross-section through the material in a direction perpendicular to the surface of the material it must be possible to distinguish the layers, e.g. by examining the cross-section under an electron microscope. During the coating process some interaction at the interface between two layers can take place, without making the layers indistinct. This is schematically shown in FIG. 1. On a substrate two regions are present, region 1 and region 2 and on each of the region a material with two distinct layers. For clarity only the parts of the material on the second region have been numbered, these parts are in fact mirrored in the material on the first region. The latter one is also indicated by the numerical 101b. On this region (101b) a material (102b) is present. This material has two layers, $CL1_B$ and $CL2_Y$ (103b, 104b). At the interface (105b) a zone is formed wherein some interaction between constituents of the two layers is present. It is however so that from layer $CL2_Y$ (104b) as from layer $CL1_B$ (103b) a large undisturbed portion is present so that both layers are distinct layers. The resulting materials are screened for performance related to a specific function or useful property, and then compared with each other to determine their relative performance with respect to the specific function or useful property.

Layer: A layer, in this invention, is part of the material and is thin in relation to its area and covers a material beneath it. A layer may or may not be thin or flat, but once it is deposited it generally covers an entire surface such that it separates the substrate below the layer or the layer on top of which it is applied from the atmosphere above the layer. A layer may be a flat, thin section of material which can have similar flat sections above and below it. The layers are thin in relation to their area and may cover all or part of the material beneath them. Layers can be applied one above the other resulting in multi-layer materials with distinct layers. The layers can be distinct due to the presence of different ingredients or substances in them, but can also refer to different physicochemical properties of equivalent materials: e.g. a layer coated from a coating solution containing gelatine, e.g., can be coated and dried so as to have a layer with a sol-like structure, but a layer coated from the same gelatine containing coating solution can be coated and dried in a second layer having a more gel-like structure, indicating that the same chemical substances can be used to coat different layers with different physicochemical properties. Layers can also be distinct in their thickness, while having been coated from the same coating solution.

When in this invention, two or more layers are to be coated on top of each other, it is possible to coat them in separate coating passages and optionally including a conditioning between all or some of the coating passages. It is then also possible to have in, e.g., a three layer material, two layers coated simultaneously in a first coating passage and the third layer in a second coating passage. Also the simultaneous coating of the three layers in a single coating passage is a possibility in the method of this invention. The way of coating the layers, depends largely on the application.

Coating solution: the layers coated in this invention are coated from a coating solution. The coating solution can be a molten film forming polymer wherein other ingredients are solved. Preferably the coating solution comprises in a solvent a polymer capable of forming a film when dried and all kinds of ingredients. The ingredients can be light-sensitive crystals, e.g. silver halide, thermosensitive compounds, organic or inorganic spacing particles, chemical compounds, e.g. surface active compounds, colorants such as pigments and dyes, softeners, hardeners, etc. The composition depends on the application. The solvent of the coating solution can be an organic solvent, mixtures of organic solvents or water, or a mixture of water and an organic solvent, e.g. a water soluble organic solvent in water. When such a mixture comprises for at least 50% by volume of water, such a solvent is termed an "aqueous" solvent.

Coating conditions: The coating conditions generally refer to physicochemical properties of the coating solutions that have to be applied to a predefined region upon said substrate. Important parameters such as surface tension, viscosity, temperature, elasticity, wet coating layer thickness, coating speed, etc. are examples of parameters describing typical coating conditions.

Drying conditions: the drying conditions describe the environmental conditions that a coated layered material "feels" between the wet-coating step and an optional final conditioning and screening step. Important parameters here include air speed, dry air temperature, air humidity, wet bulb temperature, viscosity increase, air flow direction, etc . . . Different conditions can be applied one after the other, e.g. first of all the temperature can be reduced and the air speed set to a rather low value. Afterwards the air temperature can be enhanced and the air speed increased so that stressed can be built up or reduced in different regions of said substrates. The term drying conditions can be regarded as a limited example of the broader term "conditioning".

Coated materials are used in many industries, e.g., ink jet receptive media, electrophotographic receptive media, photographic films, conductive films, food products such as biscuits and chocolates, paper products, such as packaging materials and paper towels, multi-layer automotive coatings, X-ray screens, cosmetic materials, diagnostic materials, etc . . . Said coating layers can be applied to a substrate in many different ways. For simple single coatings a single 1-layer application technique is sufficient. For more complex coatings, comprising multiple coating layers, the coating technology can become much more complicated. Methods for coating a single layer can be used in order to get a multi-layer coating when several single layers are coated on top of each other. A method making it possible to coat multiple layers simultaneously on top of each other can be advantageously used for preparing multi-layer coated materials.

Those skilled in the art are familiar with different single layer methods known in the field. These single layer methods include spin coating, dip coating, rod coating, knife coating, blade coating, air knife coating, gravure coating, forward and reverse roll coating, and slot and extrusion coating. Multi-layer coating methods comprise slide coating, cascade coating and curtain coating, both of which are very well known to those skilled in the photographic industry. Multi-layer coating methods also comprise screen printing techniques, flexographic printing techniques, electrostatographic printing techniques such as electrophotography, electrostatic technology and DEP-printing, etc . . . .

For fabrication purposes, the optimal coating technology is chosen for an optimal coating composition. Some key parameters tend to determine the best coating method: the number of layers, the wet layer thickness, the viscosity and viscoelasticity of the coating solution, the required coating accuracy, the coating support and web, and the coating speed mostly imply using only a single coating method out of the list mentioned above. Other factors that also can play a role in determining the coating method include: the dried layer coating weight, the solvent system, the viscosity response to temperature, the preferred coating temperature, the binder system, the solids loading, the surface treatment, and perhaps much more additional parameters.

For screening purposes it is advantageous to have coating methods that make it possible to have a material with coated layer(s) in a very short period of time. Preferably a coating method that gives materials with properties correlating well with the properties which would have been reached using fabrication technology coating methods is used.

In this invention a method for speeding up the process of finding ideal coating compositions for materials that have to reach the market in a short period of time, is disclosed that applies the ideas around Combinatorial Chemistry with a coating process, i.e. perform different coatings with differing compositions simultaneously on a small sample scale so that on a rather small sample different conditions are realised that can be screened for useful properties using high throughput screening methods.

The invention thus encompasses a method for developing layered materials, comprising the steps of :

applying, on a first region, $R_M$, of a substrate, a first layered material, $MR_M$, and on a second region, $R_N$, of said substrate a second layered material, $MR_N$, said material, $MR_M$, being different from said material, $MR_N$, and screening said materials, $MR_M$ and $MR_N$, for a useful property. Preferably said layers are applied by coating from a coating solution and even more preferably said coating proceeds from an aqueous coating solution by a method selected from the group consisting of dip coating, rod coating, knife coating, blade coating, air knife coating, gravure coating, forward and reverse roll coating, slot coating, extrusion coating, slide coating, cascade coating and curtain coating. Although the method of this invention for speeding up the development of layered materials can beneficially be used for the development of single layer materials, it is how ever especially useful for speeding up the development of materials, $MR_M$ and $MR_N$, comprising at least two distinct layers on top of each other. Thus in this method at least two layers, $CL1_A$ and $CL1_B$, are coated on two different regions of the substrate and at least one further layer, $CL2_Z$, on top of said layer, $CL1_A$ and at least one further layer, $CL2_Y$, on top of said layer, $CL1_B$.

When the method of this invention is used for rapid screening of materials with two distinct layers, then these two distinct layers can be coated simultaneously or one after another in separate coating passages with an optional conditioning step in between. When the method of this invention is used for rapid screening of materials with more than two distinct layers, then it is possible to have all of the layers coated simultaneously, or only some of them and the further layer(s) one after another. In such a case the optional conditioning step can be included between all coating passages, between some of the coating passages. The way the materials are coated is dependent on the application, e.g., when the method is used for rapid screening photographic materials with up to 10 or more layers, then the coating sequence in the method of this invention are largely determined by the coating sequence that normally is used in the manufacturing plant of the material.

In a method according to this invention it can be beneficial to create a reference point on the substrate during or before the coating of the layers adjacent to the substrate and to coat the further layers on top of the layers adjacent to the substrate while they are aligned in accordance with said reference point.

In the method of this invention the multiple layers, of layers of a material, can be coated so has to have them in the same direction. It is also possible to coat some of the layers in a first direction and some of the other layers so that at least some of the layers form an angle between 10 and 170° between them.

In the further paragraphs the invention will be described in detail for materials with only two layers, it is however clear that within the scope of the invention, a method for rapid screening of the properties of material with multiple layers by creating a number, larger than 1, of such materials on a single substrate, all possible coating sequences can be used as long as they serve the purpose of creating a number, larger than 1, of such materials on a single substrate.

In a first embodiment of the present invention a typical blade coating machine is used having 4 separate coating heads mounted on a straight line, for coating—from 4 different coating solutions—4 neighbouring single layers on a single receiving substrate. The layers are dried and the properties thereof are screened.

In a second embodiment of the present invention a typical coating machine is used having 4 separate cascade coating heads, each having two coating slits, mounted on a straight line for coating, from 8 different coating solutions, 4 neighbouring double layers on a single receiving substrate. Each layer contains different components in a fixed concentration. The layers are dried and the properties thereof are screened.

In a third embodiment of the present invention a typical blade coating machine is used having 4 separate coating heads mounted on a straight line , for coating, from 4 coating solutions with different composition but each with a polymer capable of forming a gel, 4 neighbouring single layers on a single receiving substrate. This is a first coating passage. The four layers are gelled (this is a conditioning step between the coating passages in the sense of this document) but not dried and using an other or the same blade coating machine 4 further single layers are coated on top of the 4 gelled layers already present on the substrate, while this second coating passage proceeds in the same direction as the first coating passage. These 4 layers are coated from 4 coating solutions having a composition that is different from each other and from each of the 4 compositions used to coat the first 4 layers. Thus 4 materials with each having two layers, wherein each of said two layers has a different composition, are present on the single substrate. The materials are dried and the properties thereof are screened. The resultant library of coated materials, for the first and second embodiment of the invention are shown in FIG. 1. In this figure the surface of the substrate (100) on which coating is performed is positioned in the plane of the paper and on 4 regions (101a, b, c, d) of the substrate 4 materials (102a, b, c, d) are present, each of the materials comprising two layers ($CL1_A$, $CL2_Z$), ($CL1_B$, $CL2_Y$), ($CL1_C$, $CL2_X$), ($CL1_D$, $CL2_W$) on top of each other, the layers, $CL1_A$, $CL1_B$, $CL1_C$, $CL1_D$, being coated closest to the substrate. The arrow A indicates the coating direction. In the figure the layers are shifted for the ease of showing the different layers, but a library according to the second or third embodiment of the invention wherein in the four materials the two layers are not shifted but coated each exactly on top of the other is within the scope of the invention.

Figure 2:
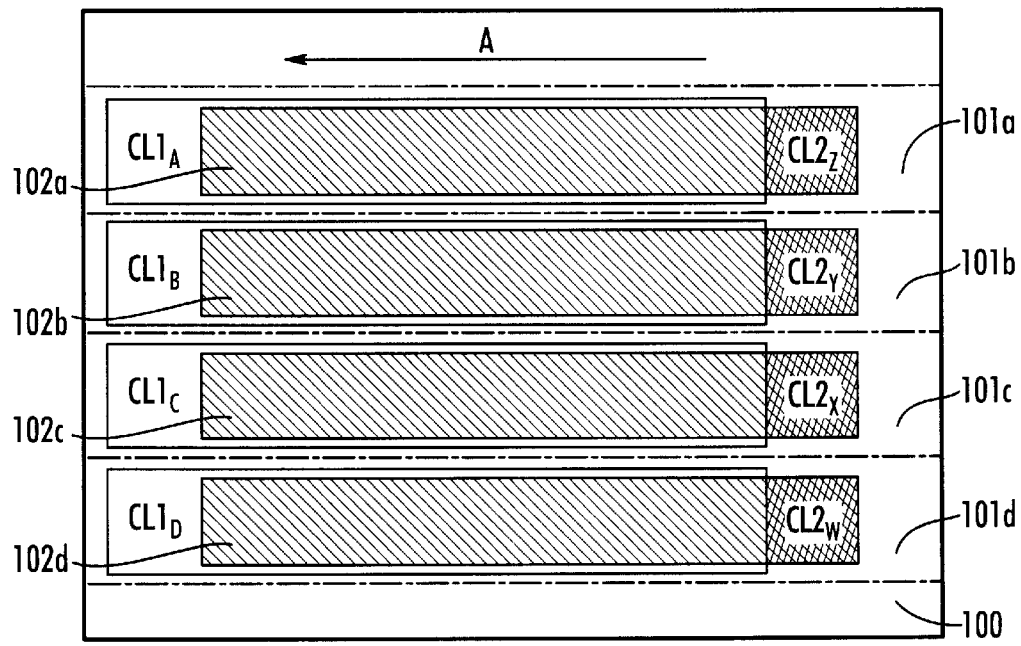
FIG. 2 shows schematically a view from the top of a multi-layer coated material coated with 4 coating variants in a single direction.
Figure 3:
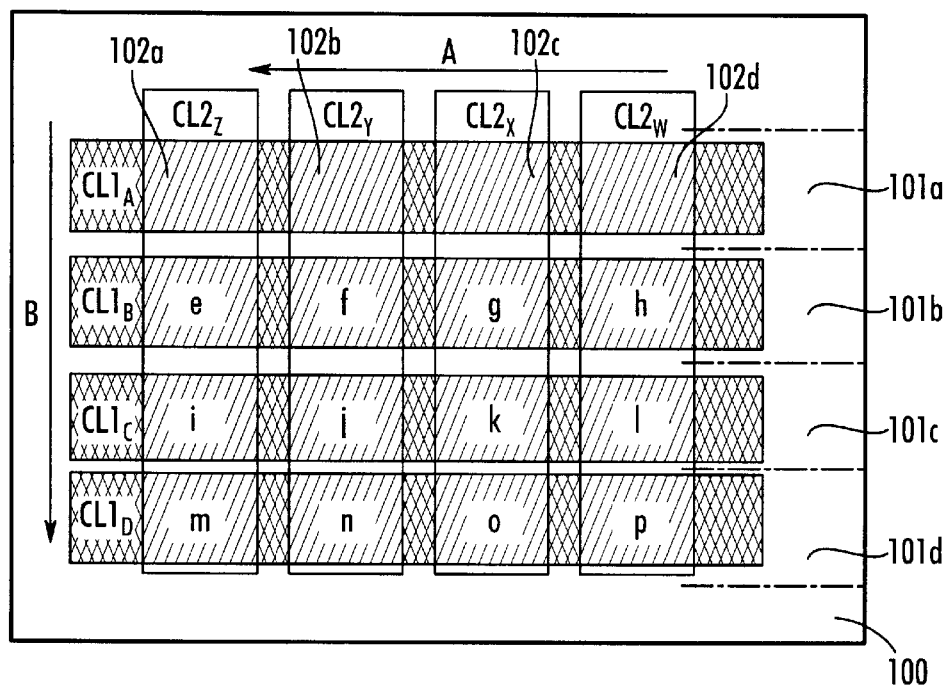
FIG. 3 shows schematically a layout of a substrate with 16 materials each with two coated layers, coated from 4 coating variants in two perpendicular directions.

In a variant of this second and third embodiment, after gelling the substrate with the four layers coated during the first coating passage, the second coating passage proceeds in a direction perpendicular to the layers already present on the single substrate. In this case, when each layer is coated from a different coating solution, in two coating passages 16 different two layer materials are prepared on a single substrate and are, after drying, ready for screening. Such a library is shown in FIG. 2. In this figure the surface of the substrate (100) on which coating is performed is positioned in the plane of the paper and on 4 regions (101a, b, c, d) of the substrate 16 materials (102a, b, c, d, e, f, g, h, i, j, k ,l, $m$, $n$, $o$) are present, each of the materials comprising two layers ($CL1_A$, $CL2_Z$), ($CL1_A$, $CL2_Y$), ($CL1_A$, $CL2_X$), ($CL1_A$, $CL2_W$), ($CL1_B$, $CL2_Z$), ($CL1_B$, $CL2_Y$), ($CL1_B$, $CL2_X$), ($CL1_B$, $CL2_W$), ($CL1_C$, $CL2_Z$), ($CL1_C$, $CL2_Y$), ($CL1_C$, $CL2_X$), ($CL1_C$, $CL2_W$), ($CL1_D$, $CL2_Z$), ($CL1_D$, $CL2_Y$), ($CL1_D$, $CL2_X$), ($CL1_D$, $CL2_W$), on top of each other, the layers, $CL1_A$, $CL1_B$, $CL1_C$, $CL1_D$, being coated closest to the substrate in a first coating passage. The arrow A indicates the coating direction of the first coating passage. The arrow B indicates the coating direction of the second passage, when the layers $CL2_Z$, $CL2_Y$, $CL2_X$, $CL2_W$ are coated. In the figure the layers are shifted for the ease of showing the different layers, but a library according to the second or third embodiment of the invention wherein in the materials the layers are not shifted but coated each exactly on top of the other is within the scope of the invention.

The coating directions in the figure are shown from right to left for arrow A and from top to bottom for arrow B. It is clear that the other possible combinations are possible as well, as long as the result is that the layers are perpendicular to each other. In this figure the coating directions are shown exactly perpendicular to each other. This a preferred embodiment, but it is possible, when needed for the application, to have the coating direction of the second coating passage adapted so that the second layer(s) in the material are positioned at an angle between 10 and 170° to the direction of the first ones.

Figure 4:
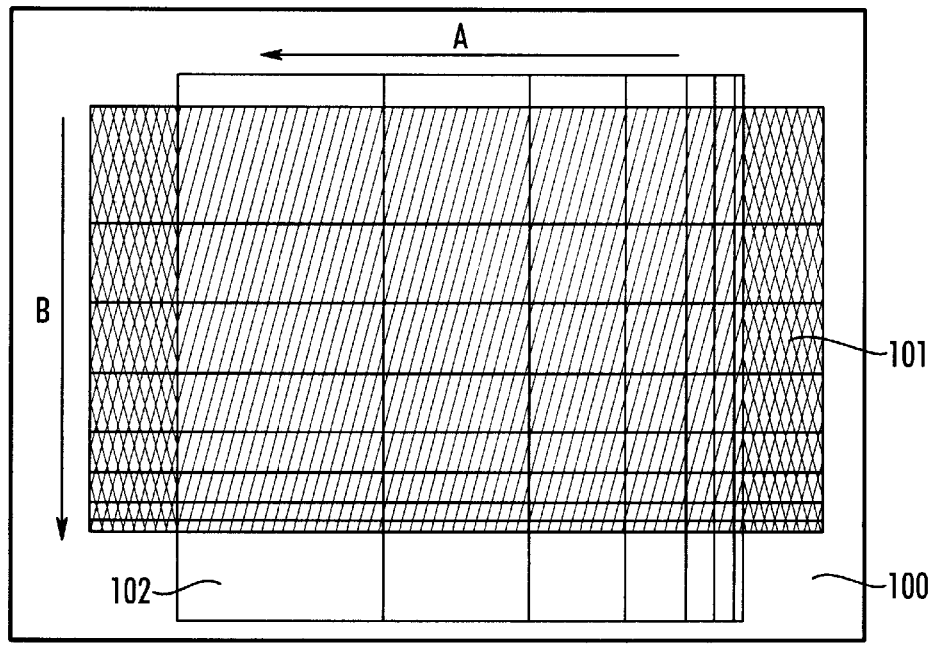
FIG. 4 shows schematically a layout of a multi-layer coated material coated with a concentration gradient for at least one coating layer perpendicular to the coating direction.

In the three embodiments described above, the layers are evenly coated, i.e. without differences in thickness or thickness gradients and the composition of the layers is constant. In a fourth embodiment of this invention the method is implemented by coating at least one layer, $CL1_A$ on a substrate, and coating at least one further layer, $CL2_Z$, on top of said layer, $CL1_A$, wherein at least one said layers $CL1_A$ and $CL2_Z$ has a continuous and/or stepwise gradient in its composition and/or thickness, forming a multi-layer material on said substrate with continuously and/or stepwise changing composition and/or thickness and screening said multi-layer material on at least two separate regions of it for a useful property. In this embodiment the two layers can be coated so that in both layers the gradient ascends in the same direction, as well as so that the gradients in the two layers are perpendicular to each other as well as so that the gradient of the second layer descends in the direction wherein the gradient of the first layer ascends. In FIG. 4 a substrate whereon a two layer material on a substrate (100) with layers, 101 and 102 is shown. Each of the layers has a continuous gradient in composition, (indicated in the figure by contour lines, the closer the contour lines the higher the concentration), and coated in a direction perpendicular to each other. The number of layers, the steepness of the gradients, etc. can be adapted to the application at hand, without departing from the scope of the invention. The gradient in thickness can easily be created when, e.g., a coating apparatus with a doctor blade is used and the distance between the doctor blade and surface of the substrate is changed during coating. This change can be made continuous or stepwise (possibly with smooth transitions). A concentration gradient can be created when during the coating one or more ingredients are continuously or step wise added to the coating solution. The advantage of this fourth embodiment of this invention resides in the fact that, when a continuously varying gradient is used, basically an infinite number of materials is formed in two coating passages, the factual number of materials depends in such a case on the spatial resolution of the screening method.

Also in this embodiment of the invention, it is possible to have any kind of conditioning included between the coating passages and/or before screening the materials.

The invention is explained above with two layer materials, but it is clear that the invention is useful for single layer materials as well as for multiple layer materials. As an example, after the first coating passage, the layers can be dried or treated with other techniques such as UV or Electron Beam (EB) curing. Said coated and dried substrate can be used for applying a second layers in a second passage. Again the receiver can be dried and more layers can be added using the same procedure.

EXAMPLES

Example 1

Development of an ink receiving material for use in Ink-jet printers.

A receiver for ink jet printing was developed using said method of combinatorial material design for a 2-layer coating upon a resin-coated paper. The first coated layer was a silica filled polyvinylalcohol layer, the top layer was a cellulose gelatine mixture or polyvinylalcohol layer, comprising no, normal or double content of ammonium polymers as mordant (polydiallyldimethyl ammonium chloride). The coating solution was adjusted to a pH value of 3, 6 or 9. A cascade coating apparatus with a coating head structure comprising three separate coating slots was used. In a first coating run said base layer comprising silica and polyvinylalcohol was applied to a resin coated paper support in 3 stripes of pH 3, 6 and 9, respectively. After drying an A4-size receiver comprising said first coated layer was used in a second coating run, but it was transported under the coating head structure at a rotation angle of 90 degrees. This second coating step was performed twice upon said first coated substrate, a first time with a gelatinous cellulose binder mixture and ammonium mordanting polymers at zero, 100% and 200% on a relative scale, and a second time with a cationic polyvinylalcohol binder and said additive at three levels. After coating and drying two A4-sheets were obtained, each having 9 separate regions of differing coating compositions. Said 18 different coating compositions were tested in an AGFA SHERPA 43 (trade name)ink jet printer and different coloured blocks were printed for judging the influence upon lightfastness and bleeding of the receivers. Therefore said 2 A4-sized receivers were placed with proper masks under a UV illumination of constant intensity (180 klux/hour) with a continuous spectrum (300–800 nm) using a high pressure xenon lamp for 24 hours, after which the samples were analysed using a full automatic KDY-image analysis system. The difference between original and illuminated densities, and a value for the bleeding between neighbouring colour patches is tabulated in table 4. From these experiments it could be concluded that said lightfastness and bleeding are determined by many interaction parameters, for which a complete understanding is not possible, and as a consequence planning of experimental set-ups without parallel analysis would lead to uncovered experimental spaces and undiscovered operational ranges.

TABLE 1 composition of first coating layer.

| EXAMPLE # | Silica (g) | Water (g) | PVA (g) | pH |
|---|---|---|---|---|
| $CL1_A$ | 1549 | 89.5 | 861.3 | 9 |
| $CL1_B$ | 991.6 | 57.3 | 551.2 | 6 |
| $CL1_C$ | 1239 | 71.6 | 689 | 3 |

The silica dispersion contained 22% (w/w) of silica particles with a mean particle diameter of 9.5 $\mu$m in 3.3% polyvinylalcohol and water. The PVA (polyvinylalcohol) is an aqueous solution containing 10% polyvinylalcohol. The wet coating thickness of this first coating layer was 109.3 µm.

TABLE 2 composition of second coating layer.

| EXAMPLE # | PVA (g) | Water (g) | Tenside (g) | Mordant (g) |
|---|---|---|---|---|
| $CL2_Z$ | 480 | 468 | 12 | 0 |
| $CL2_Y$ | 480 | 438 | 12 | 30 |
| $CL2_X$ | 480 | 408 | 12 | 60 |

PVA indicates an aqueous solution of 10% (w/w) cationic polyvinylalcohol. The tenside (a surface active component) was a 5% (w/w) solution of CTAB in water. The mordant was polydiallyldimethylammonium chloride.

For the second run of the second coating layer the compositions of table 3 were used.

TABLE 3

Composition of second coating layer for second run.

| EXAM. # | Gelatin | Water | CE | Cat-CE | Tenside | Mordant |
|---|---|---|---|---|---|---|
| $CL2_T$ | 11.3 | 464.6 | 405 | 15.3 | 18 | 0 |
| $CL2_S$ | 13.8 | 533.4 | 495 | 18.7 | 22 | 34.4 |
| $CL2_R$ | 11.3 | 408.4 | 405 | 15.3 | 18 | 56.3 |

The gelatin weight is expressed in grams. CE is a 5% (w/w) aqueous solution of a cellulose-ether. The tenside was a 5% (w/w) solution of CTAB in water. The mordant was polydiallyldimethylammonium chloride and a 5% (w/w) aqueous solution of a cationic cellulose-ether [cat-CE].

The results of the printing analysis are given in table 4.

TABLE 4

| # | pH | Gel/PVA | Mordant | LF | BL |
|---|---|---|---|---|---|
| 1 | 3 | P | 0 | 8.9 | 340 |
| 2 | 3 | P | 100 | 9.6 | 346 |
| 3 | 3 | P | 200 | 10.3 | 350 |
| 4 | 6 | P | 0 | 7.8 | 362 |
| 5 | 6 | P | 100 | 8.3 | 370 |
| 6 | 6 | P | 200 | 9.1 | 373 |
| 7 | 9 | P | 0 | 7.1 | 350 |
| 8 | 9 | P | 100 | 6.7 | 349 |
| 9 | 9 | P | 200 | 6.5 | 345 |
| 10 | 3 | G | 0 | 7.5 | 355 |
| 11 | 3 | G | 100 | 8.9 | 330 |
| 12 | 3 | G | 200 | 10.9 | 335 |
| 13 | 6 | G | 0 | 4.5 | 345 |
| 14 | 6 | G | 100 | 8.6 | 334 |
| 15 | 6 | G | 200 | 10.3 | 320 |
| 16 | 9 | G | 0 | 3.7 | 255 |
| 17 | 9 | G | 100 | 5.2 | 290 |
| 18 | 9 | G | 200 | 6.1 | 290 |

Lightfastness (LF) is expressed as a percentage change of the mean original image density (mean value of CMYK-blocks) after irradiation compared to the original one.
LF = ((C2 − C1) + (M2 − M1) + (Y2 − Y1) + (K2 − K1))/(C1 + M1 + Y1 + K1)*100 with C2 = density of cyan block after irradiation and C1 = density of cyan block before irradiation, etc . . .
Bleeding (BL) is expressed as a number indicating image noise as a result of ink coalescence on an arbitrary scale (100 = best value).

Example 2

Development of Conductive Coatings.

In another experimental set-up conductive coatings were developed using PEDT in PSS as binder system. Therefore a first layer of four different coatings was applied to four regions of a polyester substrate. In a second run four additional coatings were applied above said first coating layer at four different regions, perpendicularly located if compared with said first set of regions. Alter drying the conductivity of said resulting 16 coating segments was determined. The results are tabulated in table 7. The coating composition is given in table 5: only a single starting solution was prepared: by adjusting the wet coating thickness of said stock solution 4 different coating layers were obtained for said first coating and 4 different coating layers were obtained for said second coating. The total coating thickness of the resulting multi-layer coating is given in table 6. It is clear from table 6 that 16 coating regions are obtained by preparing only a single coating solution and parallel coating said solution (with wet coating thickness adjustment) in only 2 runs.

TABLE 5

Coating composition

| Component | Amount (g) |
|---|---|
| 1.2% solution of conductive polymer (3,4 poly-ethylene dioxy thiophene/polystyrene-sulphonic acid weight ratio 1/2.5) | 325.41 |
| 27.5% latex co(vinylidenechloride/methacrylate/itaconic acid 88/10/2) | 6.54 |
| 5% FLUORAD FC430 (trade name of 3M) | 4.20 |
| N-methyl-pyrrolidone | 39.37 |
| Glycidyl oxy propyl trimethoxysilane | 1.97 |
| Water | 672.51 |

TABLE 6

Total amount of coating weight (in $g/m^2$)

| Layers | $CL1_A$ | $CL1_B$ | $CL1_C$ | $CL1_D$ |
|---|---|---|---|---|
| $CL2_Z$ | 0.5 | 1.1 | 1.7 | 2.3 |
| $CL2_Y$ | 1.2 | 1.8 | 2.4 | 3.0 |
| $CL2_X$ | 1.9 | 2.5 | 3.1 | 3.7 |
| $CL2_W$ | 3.2 | 3.8 | 4.4 | 5.0 |

TABLE 7

Conductivity of coated film (in ohm/square)

| Layers | $CL1_A$ | $CL1_B$ | $CL1_C$ | $CL1_D$ |
|---|---|---|---|---|
| $CL2_Z$ | 7300 | 2300 | 1300 | 890 |
| $CL2_Y$ | 2100 | 1000 | 810 | 680 |
| $CL2_X$ | 940 | 760 | 665 | 520 |
| $CL2_W$ | 630 | 490 | 425 | 375 |

It must be clear for those skilled in the art that slight modifications to this basic concept of using coating technologies in a parallel way to fasten up experimental set-ups and analyses for material design, fall within the scope of the present invention. It is e.g. equally well possible to use a single layer coating technique to apply a first coating layer to a substrate at different substrate regions, followed by applying a second coating layer to said substrate at top of said first coating layer but rotated at an angle of 120 degrees, followed by applying a third coating layer to said substrate on top of said first and second layer but applied with a rotation of 240 degrees. Afterwards different regions with three-layer structures can be screened for useful properties. Coating methodologies coating different coatings to different regions upon a substrate in one dimension, and over coating said coated material in the same direction but with a certain translation perpendicular to the coating direction, falls also under the scope of the present invention. Also the combination of coating different bands in one direction with a concentration gradient in the other direction, falls under the scope of the present invention. A combination of different bands with varying layers in the coating direction, followed by consecutive different bands with other varying layers in the same coating direction, also falls under the scope of the present invention.

What is claimed is:

1. A method for developing layered materials, comprising the steps of:

applying, on a first region, $R_M$, of a substrate, a first layered material, $MR_M$, and on a second region, $R_N$, of said substrate a second layered material, $MR_N$, said material, $MR_M$, being different from said material, $MR_N$, and screening said materials, $MR_M$ and $MR_N$, for a useful property, wherein said layers are applied by coating solution;

wherein said materials, $MR_M$ and $MR_N$, comprise at least two distinct layers;

wherein at least two of said at least two distinct layers are coated in separate coating passages and at least one conditioning step is included between said coating passages;

wherein in at least two of said separate coating passages coating proceeds in directions so that layers coated during said separate coating during said coating passages form an angle between 10 and 170° with each other.

2. A method according to claim 1 wherein said conditioning step is a step of drying said layers under controlled temperature and relative humidity.

3. A method according to claims 1, wherein a reference point on the substrate is created during a first of said separate coating passages and further layers are coated during further coating passages in alignment with said reference point.

4. A method according to claims 2, wherein in a reference point on the substrate is created during a first of said separate coating passages and further layers are coated during further coating passages in alignment with said reference point.

* * * * *